United States Patent
Lambrecht et al.

(10) Patent No.: US 9,086,419 B2
(45) Date of Patent: Jul. 21, 2015

(54) GDF15 AS A DIFFERENTIAL MARKER FOR SPONDYLOARTHROPATHY

(75) Inventors: Stijn Lambrecht, Landskouter (BE); Dieter Deforce, Kuurne (BE); Dirk Elewaut, Heusden (BE); August Verbruggen, Nazareth (BE)

(73) Assignee: Universiteit Gent, Ghent (BE)

( * ) Notice: Subject to any disclaimer, the term of this patent is extended or adjusted under 35 U.S.C. 154(b) by 145 days.

(21) Appl. No.: 13/201,912

(22) PCT Filed: Feb. 17, 2010

(86) PCT No.: PCT/EP2010/051992
§ 371 (c)(1),
(2), (4) Date: Aug. 17, 2011

(87) PCT Pub. No.: WO2010/094709
PCT Pub. Date: Aug. 26, 2010

(65) Prior Publication Data
US 2011/0300562 A1 Dec. 8, 2011

(30) Foreign Application Priority Data
Feb. 19, 2009 (GB) .................. 0902737.6

(51) Int. Cl.
*G01N 33/53* (2006.01)
*G01N 33/68* (2006.01)

(52) U.S. Cl.
CPC ...... *G01N 33/6887* (2013.01); *G01N 2800/102* (2013.01)

(58) Field of Classification Search
None
See application file for complete search history.

(56) References Cited

FOREIGN PATENT DOCUMENTS

| WO | 99/06445 A1 | 2/1999 |
|---|---|---|
| WO | 01/81928 A1 | 11/2001 |
| WO | 2007/089303 A2 | 8/2007 |

OTHER PUBLICATIONS

Cruyssen et al. (2005) Ann. Rheum. Dis 64:1145-1149.*
Illopoulos et al., "Integrative MicroRNA and Proteomic Approaches Identify Novel Osteoarthritis Genes and Their Collaborative Metabolic and Inflammatory Networks", PlosOne, vol. 3, Issue 11, pp. Nov. 2008.
Noorali et al., "Dynamics of expression of growth differentiation factor 15 in normal and PIN development in the mouse", Differentiation 75, pp. 325-336, 2007.
Search Report and Written Opinion pertaining to International Application No. PCT/EP2010/051992 dated Jun. 16, 2010.

* cited by examiner

*Primary Examiner* — Michael Pak
(74) *Attorney, Agent, or Firm* — Dinsmore & Stohl LLP

(57) ABSTRACT

In vitro methods for differential diagnosis of spondyloarthropathy are disclosed which involve determining the levels of GDF15 in biological samples.

8 Claims, 5 Drawing Sheets

GDF15 AS A DIFFERENTIAL MARKER FOR SPONDYLOARTHROPATHY

Methods for diagnosing spondyloarthropathy are disclosed which involve determining levels of GDF15 in a synovial fluid sample or a blood serum sample.

BACKGROUND OF THE INVENTION

The transforming growth factor-β (TGF-β) superfamily consists of an increasing number of molecules that regulate a variety of cellular processes such as growth, differentiation and oncogenesis. Members of the TGF-β superfamily have been classified into major family groupings, which include TGF-β, morphogenic proteins (MP), bone morphogenic proteins (BMP), osteogenic proteins (OP), growth and differentiation factors (GDF), inhibins/activins, mullerian inhibitory substances (MIS) and glial derived neurotrophic factors (GDNF). TGF-β was first characterised for its effects on cell proliferation. It both stimulated the anchorage-independent growth of rat kidney fibroblasts and inhibited the growth of monkey kidney cells. TGF-β family members have been shown to have many diverse biological effects, e.g. they regulate bone formation, induce rat muscle cells to produce cartilage-specific macromolecules, inhibit the growth of early haematopoietic progenitor cells, T cells, B cells, mouse keratinocytes, and several human cancer cell lines. TGF-β family members increase the synthesis and secretion of collagen and fibronectin, accelerate healing of incisional wounds, suppress casein synthesis in mouse mammary explants, inhibit DNA synthesis in rat liver epithelial cells, stimulate the production of bFGF binding proteoglycans, modulate phosphorylation of the epidermal growth factor ("EGF") receptor and proliferation of epidermoid carcinoma cells and can lead to apoptosis in uterine epithelial cells, cultured hepatocytes and regressing liver. TGF-βs can mediate cardio-protection against reperfusion injury by inhibiting neutrophil adherence to endothelium and protect against experimental autoimmune diseases in mice. On the whole, proteins of the TGF-β family are multifunctional, active growth factors and also have related biological activities such as chemotactic attraction of cells, promotion of cell differentiation and tissue-inducing capabilities. Differences in their structure and in their affinity for receptors lead to considerable variations in their exact biological function.

Proteins of the TGF-β family are synthesized as large, inactive precursor (pro-form) proteins, which are proteolytically processed at a dibasic site (RXXR) to generate the mature, active form of the protein.

Growth differentiation factor 15 is a distant member of the TGF-β family. The expression of the mature form of growth differentiation factor 15 (GDF15) protein is associated with early prostate carcinogenesis. GDF15 has been described in the literature as macrophage inhibitory cytokine-1 (MIC-1), placental bone morphogenic protein (PLAB), placental transforming growth factor-β (PTGF-β), prostate derived factor (PDF), and non-steroidal anti-inflammatory activated gene-1 (NAG-1) reflecting the different functions that has been implied for this protein.

WO2001081928 published on 1 Nov. 2001 discloses diagnostic assays, and methods of treatment involving GDF15, and WO1999006445 published on 11 Feb. 1999 discloses the GDF15 polynucleotide sequence and amino acid sequence.

In earlier studies on GDF15 expression in human normal and prostate cancer cells, it was found that the level of GDF15 transcript does not necessarily correlate well with that of the GDF15 protein (Noorali et al. Differentiation (2007) 75: 325-336). The reasons for these discrepancies could be due to differences in post-transcriptional modifications or processing of RNA, that influences its stability or translation, or post-translational modifications of the protein affecting protein maturation, accumulation or degradation.

As indicated above, GDF-15 may have applications in the treatment of immunologic disorders. In particular, GDF-15 may be used as an anti-inflammatory agent or as a treatment for disorders related to abnormal proliferation or function of lymphocytes.

Many forms of inflammatory rheumatic diseases are autoimmune disorders, in which the body views its own tissues as foreign and reacts with inflammation. These autoimmune conditions include rheumatoid arthritis and Spondyloarthropathy Rheumatoid arthritis (RA) is an autoimmune disease, which causes chronic inflammation of the joints, the tissue around the joints, as well as other organs in the body. Patients with these diseases have antibodies in their blood, which target their own body tissues, where they can be associated with inflammation. Because it can affect multiple other organs of the body, rheumatoid arthritis is referred to as a systemic illness and is sometimes called rheumatoid disease. While rheumatoid arthritis is a chronic illness (meaning it can last for years) patients may experience long periods without symptoms.

Brown et al. (Arthritis & Rheumatism (2007) 56: 753-764) demonstrated that GDF15 serum levels were enhanced in rheumatoid arthritis and reflected disease severity independently of classic disease markers. Variation in serum levels of GDF15 with disease severity, reduction in levels with successful treatment, the association of allelic variations with erosive disease and treatment resistant RA, and the local expression of GDF15 in rheumatoid synovium strongly supported the notion of a role for this cytokine in the pathogenesis of RA Spondyloarthropathy (SpA) is the name given to a group of chronic or long lasting diseases also called Spondyloarthritis or Spondylitis. These diseases are forms of inflammatory arthritis that primarily affect the spine, although other joints and organs can become involved. Until now no laboratory tests that are specific for ankylosing spondylitis have been developed.

Osteoarthritis (OA) is a complex, multifactorial, age-dependent degenerative disease of the synovial joints. It affects females at a higher rate than males, particularly after the menopause. OA is characterized by changes to all the components of the joint, with degeneration and loss of articular cartilage and changes to the subchondral bone being constant factors in disease progression. Along with the breakdown of the cartilage and joint space narrowing, there is thickening and sclerosis of the subchondral bone, development of cysts and bony outgrowth at the margins of the joint. Despite an increase in bone volume fraction, the subchondral bone is mechanically weaker in OA because of hypomineralization, increased collagen metabolism and altered bone remodeling. In a report of Hopwood et al. (Arthritis Research & Therapy (2007) 9: R100), microarray gene expression profiling of osteoarthritic bone suggests altered TGF-β/BMP signaling. GDF15 gene expression was downregulated in OA when compared with control bone.

A recent report of Iliopoulos et al (PLoS ONE (2008) 3:e3740) describes that GDF15 is a differential expressed protein between osteoarthritic and normal chondrocytes.

Differentiated inflammatory rheumatic diseases such as RA and SpA are both characterized by articular cartilage defects and persistent joint inflammation that can lead to severe, chronic pain, discomfort and functional disability. Particularly in the early phases of disease, it is often difficult to fulfill the diagnostic or classification criteria of either of these diseases, and therefore the term undifferentiated arthritis is used. When the disease has only clinically manifested itself for a short period of time, the term early arthritis is used. Patients who cannot be classified as having a well-defined arthropathy that appeared only within a short time frame typically are labeled as having early-undifferentiated arthritis. Over time, some patients develop sufficient features to permit classification, whereas others remain undifferentiated.

Therefore, there is a particular need for a marker that allows an early and easy differential diagnosis of SpA from other inflammatory rheumatic diseases, or from RA within the group of inflammatory rheumatic disease or to identify the subset of patients having early undifferentiated arthritis destined to develop RA or SpA. This is important for choosing appropriate treatment strategies, to avoid (further) irreversible joint destructions and function-loss and to provide a good quality of life.

The above problem is solved by the present invention. GDF15 is a secreted protein, which makes it easy to measure it in biological samples without the need to collect cells.

SUMMARY OF THE INVENTION

The invention provides for the use of GDF15 as an in vitro marker to differentiate Spondyloarthropathy (SpA) from other inflammatory rheumatic diseases, such as for example Rheumatoid Arthritis (RA) or to predict the development of SpA or RA from undifferentiated arthritis. More in particular the invention provides the use of GDF15 as an in vitro marker to differentiate SpA from RA, or to predict the development of SpA from undifferentiated arthritis. The present invention also provides the above-described use of GDF15 in a marker panel.

In an embodiment, the present invention provides for an in vitro method to differentiate SpA from RA or to differentiate Spa or RA from undifferentiated arthritis, said method comprising determining the amount of the molecular marker GDF15 present in a biological sample and correlating said determined amount to the presence or development of SpA. In addition said method can further comprise comparing said determined amount against the range of amounts of GDF15, present in normal or reference biological samples. The biological sample can be a blood serum sample and/or a synovial fluid sample. The amount of GDF15 present in the biological sample can be determined by an immunoassay using antibodies or fragments thereof against GDF15.

In an aspect of the invention the determination of GDF15 is combined with the detection of one or more markers for inflammatory rheumatic diseases. Said one or more markers for inflammatory rheumatic diseases can for example be, a rheumatoid factor or/and an antibody against citrullinated peptides.

DETAILED DESCRIPTION

Figure 1A:
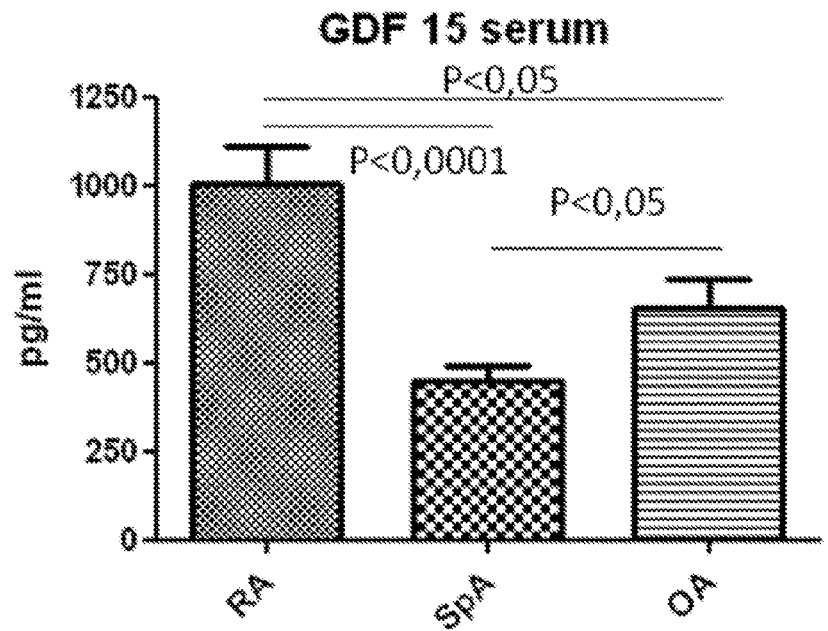
FIG. 1A & B: Concentration of GDF15 in blood serum samples from patients diagnosed with RA, SpA and OA respectively.
Figure 1B:
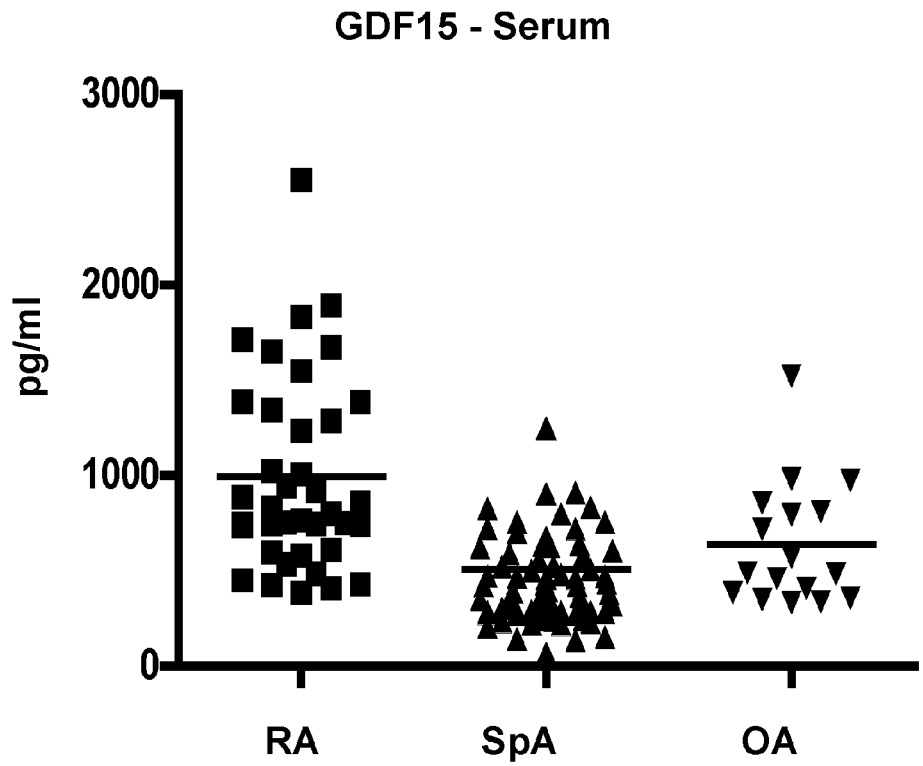

The spondyloarthropathies (SpAs) are a family of related disorders that include but are not limited to ankylosing spondylitis (AS), reactive arthritis (ReA; also known as Reiter syndrome [RS]), psoriatic arthritis (PsA), spondyloarthropathy associated with inflammatory bowel disease (IBD), undifferentiated spondyloarthropathy (USpA), and, possibly, Whipple disease and Behcet disease Ankylosing spondylitis, which literally means "inflamed spine growing together," is the prototypical spondyloarthropathy.

Differentiated inflammatory rheumatic diseases such as RA and SpA are both characterized by articular cartilage defects and persistent joint inflammation that can lead to severe chronic pain, discomfort and functional disability. Patients who cannot be classified as having a well-defined arthropathy with recent onset typically are labeled as having early-undifferentiated arthritis or early arthritis. Some patients develop sufficient features to permit classification, whereas others remain undifferentiated.

In an embodiment, the present invention provides for the use of GDF15 as an in vitro marker to differentiate Spondyloarthropathy (SpA) from other inflammatory rheumatic diseases, such as for example Rheumatoid Arthritis (RA), or to predict the development of SpA or RA from undifferentiated arthritis, more in particular as an in vitro marker to differentiate or predict the development of SpA from undifferentiated arthritis.

The term "a biological sample" includes but is not limited to serum, blood, synovial fluid, saliva, sputum, urine, fecal matter or tissue. Methods of obtaining biological samples from subjects are known in the art and are not described herein in detail.

As used herein the "GDF15" polypeptide is meant to be a protein encoded by a mammalian gdf15 gene (other names micl, plab, ptgf-B, pdf or nag-1 gene), including allelic variants as well as biologically active fragments thereof containing conservative or non-conservative changes as well as artificial proteins that are substantially identical, i.e. 70%, 75%, 80%, 85%, 87%, 89%, 90%, 92%, 93%, 94%, 95%, 96%, 97%, 98%, or 99% identical to any one of the aforementioned GDF15 polypeptides. In a particular embodiment the GDF15 polypeptide is 70%, 75%, 80%, 85%, 87%, 89%, 90%, 92%, 93%, 94%, 95%, 96%, 97%, 98%, or 99% identical to the human GDF15 (encoded by Genbank Accession NM_004864 (mRNA) or NC_000019.8 (genomic)). Within the meaning of this term, GDF15 encompasses all proteins encoded by a gdf15 gene, mutants thereof, alternative splice proteins thereof, fragments thereof and glycosylated proteins thereof, and other post translational modifications thereof.

By analogy, the "GDF15" polynucleotide is meant to include allelic variants as well as biologically active fragments thereof containing conservative or non-conservative changes as well as any nucleic acid molecule that is substantially identical, i.e. 70%, 75%, 80%, 85%, 87%, 89%, 90%, 92%, 93%, 94%, 95%, 96%, 97%, 98%, or 99% identical to any one of the aforementioned GDF15 encoding polynucleotides. In a particular embodiment the GDF15 polynucleotide is 70%, 75%, 80%, 85%, 87%, 89%, 90%, 92%, 93%, 94%, 95%, 96%, 97%, 98%, or 99% identical to the nucleic acid molecule encoding for human GDF15 (Genbank Acession No. NM_004864 (mRNA) or NC_000019.8 (genomic)).

As used herein, the terms "polynucleotide" and "nucleic acid" are used interchangeably to refer polynucleotides of any length, either deoxyribonucleotides or ribonucleotides or analogs (e.g., inosine, 7-deazaguanosine, etc.) thereof "Oligonucleotides" refer to polynucleotides of less than 100 nucleotides in length, preferably less than 50 nucleotides in length, and most preferably about 10-30 nucleotides in length. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can include modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

"Polypeptide" refers to any peptide or protein comprising amino acids joined to each other by peptide bonds or modified peptide bonds. "Polypeptide" refers to both short chains, commonly referred to as peptides, oligopeptides or oligomers, and to longer chains, generally referred to as proteins. Polypeptides may contain amino acids other than the 20 gene-encoded amino acids.

"Polypeptides" include amino acid sequences modified either by natural processes, such as post-translational processing, or by chemical modification techniques which are well known in the art. Such modifications are well described in basic texts and in more detailed monographs, as well as in a voluminous research literature.

Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications (see, for instance, Proteins-Structure and Molecular Properties, 2nd Ed., T. E. Creighton, W.H. Freeman and Company, New York, 1993; Wold, F., Post-translational Protein Modifications: Perspectives and Prospects, pgs. 1-12 in Postranslational Covalent Modification of Proteins, B. C. Johnson, Ed., Academic Press, New York, 1983; Seifter et al., "Analysis for protein modifications and nonprotein cofactors", Meth Enzymol (1990) 182: 626-646 and Rattan et al., "Protein Synthesis: Post-translational Modifications and Aging", Ann NY Acad Sci (1992) 663: 4842).

With "differential marker" or "marker" is meant a polypeptide and modifications thereof that distinguishes a group of subjects or samples from another group of subjects or samples.

The invention also concerns an in vitro method to differentiate SpA from RA or from undifferentiated arthritis, said method comprising determining the amount of the GDF15 present in a biological sample and correlating said determined amount to the presence or development of SpA. In this method the determined amount can be differentially compared to the range of amounts of GDF15, present in biological samples from subjects having osteoarthritis, rheumatoid arthritis or inflammatory rheumatic diseases. Thus, the amount of GDF15 present in a biological sample of a patient can be compared to normal or reference biological samples. For example, when the amount of GDF15 of a patient is determined in a serum sample it can be compared to the amount of GDF15 in serum samples from healthy subjects (normal sample). In another example the amount of GDF15 in a synovial fluid sample from a subject suspected of having spondyloarthropathy, can be compared to samples from subjects not having an inflammatory rheumatic disease such as healthy subjects or subjects with OA (reference sample).

Hence in an embodiment of the invention the method as described above, further comprises comparing said determined amount against the range of amounts of GDF15, present in normal or reference biological samples.

As the skilled artisan will appreciate, the differentiation between SpA and RA or between SpA and undifferentiated arthritis is made in vitro. Consequently, the patient sample is merely used for the in vitro method of the invention. The amount of GDF15 can be determined in more than one biological sample. More in particular the amount of GDF15 can be determined in one, two or more samples from the same test subject. Typically, the sample is a liquid sample. Preferably, the biological sample is a blood serum sample or a synovial fluid sample.

The amount of GDF15 present in the one, two or more biological samples or the ratio of the amount of GDF15 present in a first and a second biological sample can be correlated to the presence or the development of spondyloarthropathy.

The first and second biological samples can be from the same fluid or tissue, e.g. they can be both serum samples or synovial fluid samples, or they can be from different fluids and tissues, e.g. they can be a serum sample and a synovial fluid sample.

Biological samples can be taken at the same time point or at different time points.

As the skilled artisan will appreciate the step of correlating a particular GDF15 level to the presence or development of SpA can be performed and achieved in different ways. In general, in each of said methodologies (assays) a reference population is selected and a reference range established. This reference range in terms of absolute values, like a given concentration, is accordingly dependent on the assay employed and the standardization used in producing the assay.

The ideal scenario for diagnosis would be a situation wherein the occurrence or presence of a single event (parameter) or process would correlate with the respective disease. In all other cases correct diagnosis can be very difficult, especially when the etiology of the disease is not fully understood, as is the case for SpA.

In said circumstances, the accuracy of the diagnostic method used, i.e. the assay with its particular GDF15 marker level, is best described by its receiver-operating characteristics (ROC). The ROC graph is a plot of all of the sensitivity/specificity pairs resulting from continuously varying the decision thresh-hold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or disease versus another disease, like in the present case.

In each case, the ROC plot depicts the overlap between the two distributions by plotting the sensitivity versus 1-specificity for the complete range of decision thresholds. On the y-axis the sensitivity, or the true-positive fraction is defined as (number of true-positive test results)/(number of true-positive+number of false-negative test results). This has also been referred to as positivity in the presence of a specific disease or condition. It is calculated solely from the affected subgroup or the subgroup having a specific disease (e.g. SpA). On the x-axis the false-positive fraction, or 1-specificity is defined as (number of false-positive results)/(number of true-negative+ number of false-positive results). It is an index of specificity and is calculated entirely from the unaffected subgroup or the subgroup having another specific disease (e.g. samples from patients with RA).

Because the true- and false-positive fractions are calculated entirely separately, by using the test results from two different subgroups, the ROC plot is independent of the prevalence of disease in the sample. Each point on the ROC plot represents a sensitivity/1-specificity pair corresponding to a particular decision threshold (e.g. a cut-off concentration of GDF15). A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45 diagonal line from the lower left corner to the upper right corner. Most plots fall in between these two extremes. (If the ROC plot falls completely below the 45 diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot. By convention, this area is always >0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

A marker does qualify as a differential marker for SpA if the area under the curve (AUC) for this marker alone, when assessing the diagnostic accuracy by comparing samples from patients with SpA versus samples of patients with RA is at least 0.65

It has been previously described that the levels of GDF15 in serum of patients with the inflammatory joint disease RA are elevated. Unexpectedly, blood serum levels of GDF15 are low in SpA while the ratios (serum/synovial fluid) GDF15 concentration in SpA patients is high when compared to RA.

The amount of GDF15 present in a biological sample may be readily determined by methods known in the art, for example, immunoassays using antibodies (monoclonal or polyclonal) or fragments thereof against GDF15. Anti-GDF15 antibodies and fragments thereof can be produced by any of the methods known in the art.

The antibodies can be bound to many different carriers and used to detect the presence of a GDF15 antigen. The nature of the carrier can be either soluble or insoluble. Examples of well-known carriers include glass, polystyrene, polypropylene, polyethylene, dextran, nylon, amylases, natural and modified celluloses, polyacrylamides, agaroses and magnetic beads. Those skilled in the art will know of other suitable carriers for binding antibodies, or will be able to ascertain such, using routine experimentation.

In addition, the antibodies in these immunoassays can be detectably labeled in various ways. Examples of types of immunoassays which can utilize antibodies are competitive and noncompetitive immunoassays in either a direct or indirect format. Examples of such immunoassays are the radioimmunoassay (RIA) and the sandwich (immunometric) assay.

There are many different labels and methods of labeling known to those of ordinary skill in the art. Examples of the types of labels, which can be used in the present invention, include enzymes, radioisotopes, fluorescent compounds, colloidal metals, chemiluminescent compounds, phosphorescent compounds, and bioluminescent compounds. Those of ordinary skill in the art will know of other suitable labels for binding to an antibody, or will be able to ascertain such, using routine experimentation.

Another technique, which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

Hence, in a method of the invention, the amount of GDF15 present in the biological sample can be determined by an immunoassay using antibodies or fragments thereof against GDF15.

Generally, various clinical symptoms and biological markers are considered together for diagnosis. Markers can either be determined individually or they can be measured simultaneously. The concentrations of the biomarkers are then interpreted independently using an individual cut-off for each marker or they are combined for interpretation.

Frequently, the combination of markers is evaluated. Preferably the values measured for markers of a marker panel, are mathematically combined and the combined value is correlated to the underlying diagnostic question. Marker values may be combined by any appropriate state of the art mathematical method.

It is a preferred embodiment of the invention to use an optimized multivariate cut-off for the underlying combination of biological markers and to discriminate state A from state B. In this type of analysis the markers are no longer independent but form a marker panel.

Rheumatoid factors (=RF) are autoantibodies directed against the constant Fc region of immunoglobulin G. It is found in inflammatory rheumatic diseases such as RA and SpA, non-rheumatic disease and even in healthy persons aged over 60 years. RF autoantibodies belong to all immunoglobulin classes and most of the assays used today do not differentiate between the isotypes IgM, IgG and IgA. More recently the RF-isotypes IgG and IgA have come into focus.

The differential marker GDF15 can be used in combination with markers for inflammatory arthritis such as but not limited to rheumatoid factor (RF) isotypes (e.g. RF-IgM and RF-IgA) and/or antibodies against citrullinated peptides. The latter include but are not limited to antibodies against the antiperinuclear factor (APF) and antibodies against keratin (AKA), in particular those targeting filaggrin. The one or more marker as indicated above may be combined with any known or future marker of SpA.

Hence in an embodiment of the invention determining GDF15 is combined with determining one or more markers for inflammatory rheumatic diseases. The inflammatory rheumatic diseases form a group of disorders that are highly variable in their phenotypic expression. However, they have in common the presence of localized and/or systemic inflammation, which results in characteristic connective tissue and internal organ damage. In particular, the one or more marker for inflammatory rheumatic disease is selected from the group consisting of a rheumatoid factor and an antibody against citrullinated peptides.

Thus the present invention also provides the use of GDF15, as an in vitro marker to differentiate SpA from RA or to predict the development of SpA or RA from undifferentiated arthritis, in a marker panel.

The agents described herein can be packaged as a kit. Thus, one or more agents can be present in a first container, and the kit can optionally include one or more agents in a second container. The kit can include instructions describing the method of the present invention. The agents, containers and/or the instructions can be present in a package.

The contents of the kit can contain but is not limited to buffers or their constituents, antibodies, multiwell plates, enzyme substrates, blocking agents, reference markers etc.

This invention will be better understood by reference to the experimental details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXPERIMENTAL PART

Example 1

Analysis of GDF15 Concentration in Blood Serum Samples

Serum samples were obtained from 121 patients. 38 Patients with RA fulfilling the American College of Rheumatology (ACR) criteria (Arnett, F. C., Edworthy, S. M., Bloch, D. A., McShane, D. J., et al., Arthritis Rheum. 1988, 31, 315-24), 67 patients with SpA fulfilling the European Spondyloarthropathy Study Group criteria (Dougados, M., van-der-Linden, S., Juhlin, R., Huitfeldt, B., et al., Arthritis Rheum. 1991, 34, 218-27) and 16 patients with osteoarthritis (OA) fulfilling the ACR criteria (Altman, R., Asch, E., Bloch, D., Bole, G., et al., Arthritis Rheum. 1986, 29, 1039-49) were included in this study. After serum isolation, the samples were immediately frozen until further use. GDF15 concentrations were measured by standard ELISA techniques using the GDF15 ELISA DuoSet (R&D systems, Abingdon, UK) according to the manufacturer's instructions.

Example 2

Analysis of GDF15 Concentration in Synovial Fluid Samples

Synovial fluid samples were obtained from 115 patients undergoing needle arthroscopy of the knee for diagnostic work-up or for therapeutic reasons. 39 Patients with RA fulfilling the American College of Rheumatology (ACR) criteria, 68 patients with SpA fulfilling the European Spondyloarthropathy Study Group criteria and 8 patients with osteoarthritis (OA) fulfilling the ACR criteria were included in this study. All patients undergoing needle arthroscopy had active synovitis (RA and SpA) or joint effusion (OA) of the knee. Samples were immediately frozen until further use. GDF15 concentrations were measured by standard ELISA techniques using the GDF15 ELISA DuoSet (R&D systems, Abingdon, UK) according to the manufacturer's instructions. Results of Example 1 and 2

GDF15 concentrations were analyzed in serum samples from RA, OA and SpA patients. As might be expected, significantly increased ($p<0.0001$) levels were found in RA patients (993.7 pg/ml+/−81.7) (FIG. 1A & B). GDF15 levels in SpA (508.21 pg/ml±64.7) were similar to healthy control levels (442.1 pg/ml+/−39.0, n=3). OA-patients showed slightly elevated levels (638.9 pg/ml+/−78.22).

Figure 2A:
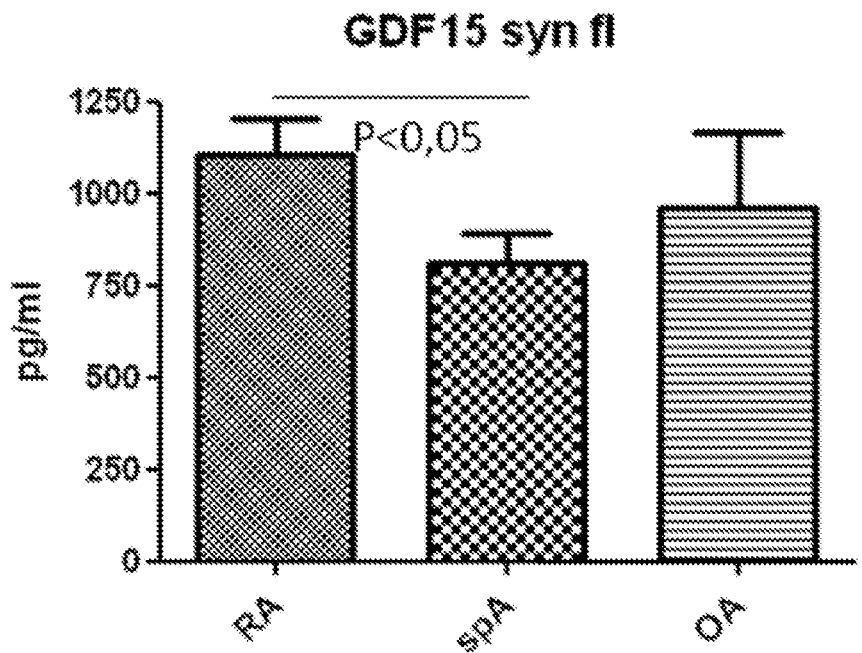
FIG. 2 A & B: Concentration of GDF15 in synovial fluid samples from patients diagnosed with RA, SpA and OA respectively.
Figure 2B:
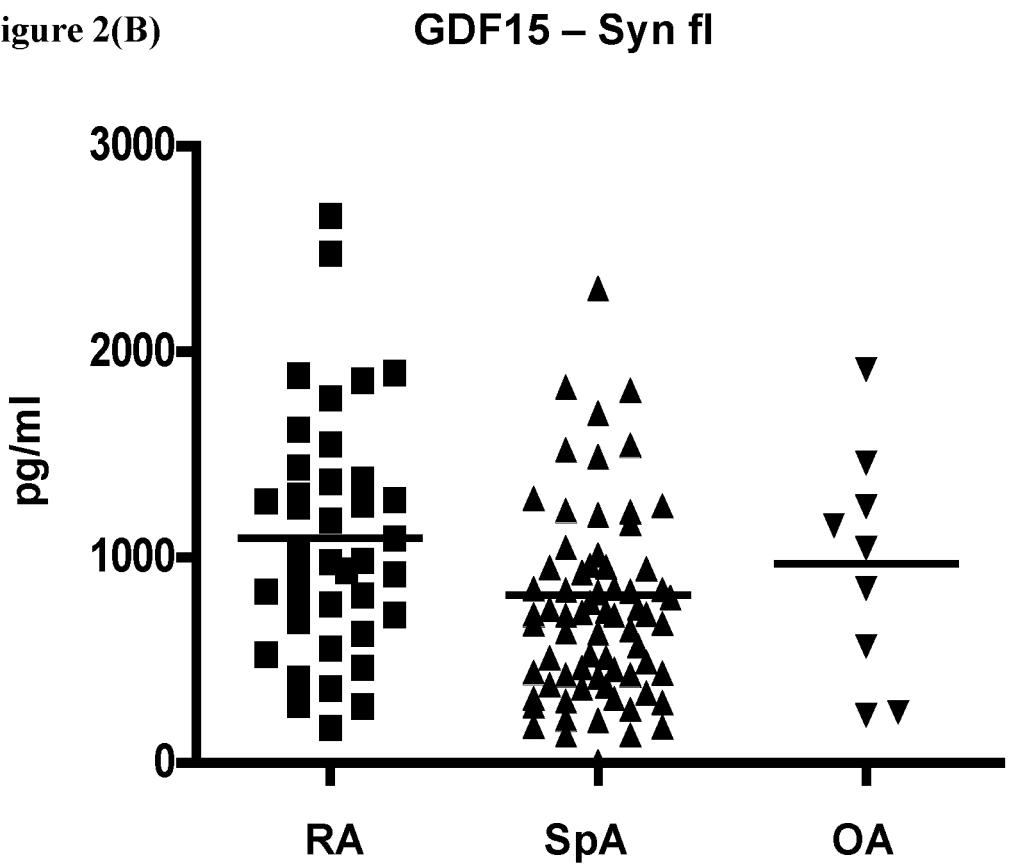

GDF15 concentrations in synovial fluid samples from RA (1094.35 pg/ml+/−92.87), SpA (815.3 pg/ml+/−89.26) and OA patients (967.7 pg/ml+/−186.0) follow the same trend (p=0.0019) (FIG. 2 A & B). In view of the fact that normal synovial fluid samples are not readily available, OA samples can be considered as being the non inflammatory controls.

Figure 3:
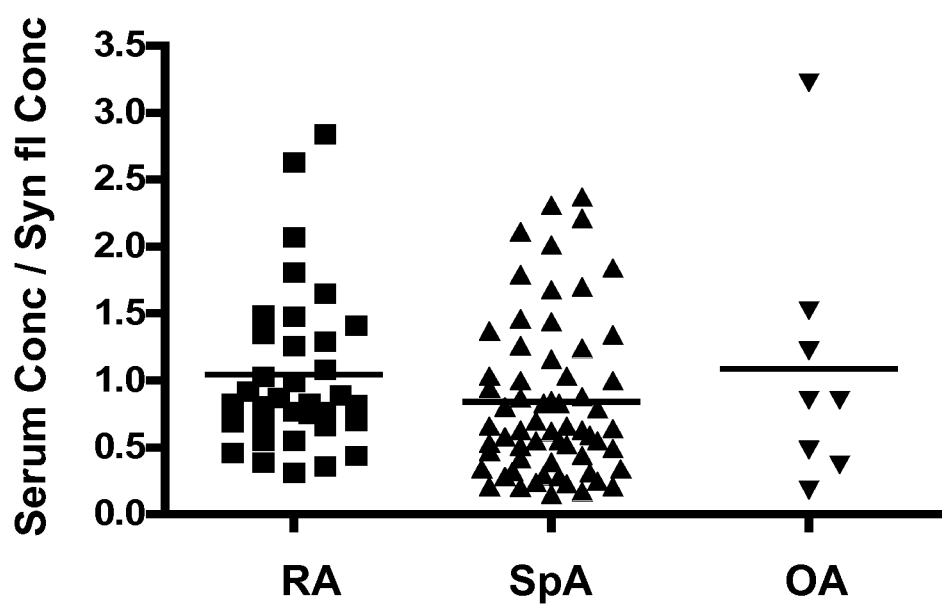
FIG. 3: ratios of GDF15 concentration (serum sample/synovial fluid)

SpA patients (0.84) showed significantly lower (p=0.03) ratios of GDF15 concentration (serum samples/synovial fluid) compared to RA patients (1.15) (FIG. 3). Hereby adding an additional way to discriminate between the two major inflammatory joint diseases SpA and RA.

The sensitivities and specificities were calculated together with the 95% confidence interval (CI). A receiver operating characteristics (ROC) curve was generated by plotting sensitivity (y axis) against 1-specificity (x axis).

Figure 4:
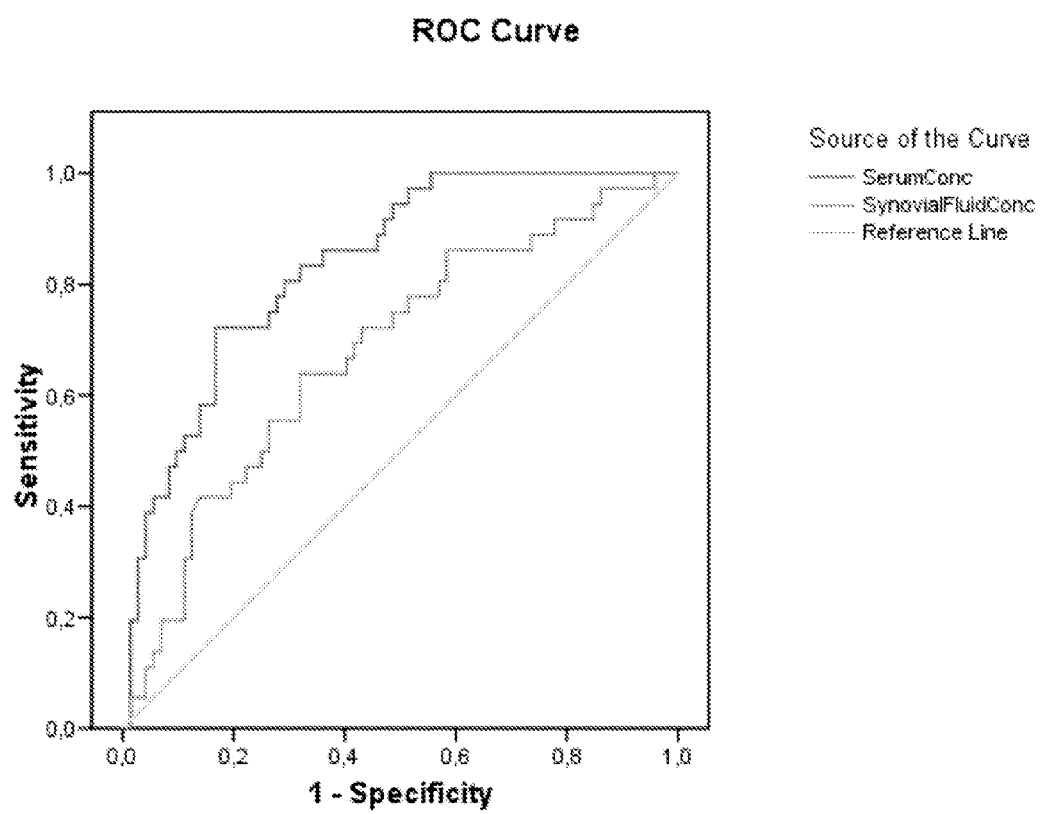
FIG. 4: ROC curve analysis for GDF15 in serum samples and synovial fluid of SpA versus RA

The AUC of the ROC curve analysis for GDF15 in serum samples of SpA versus RA (FIG. 4) is 0.837 (95% CI, 0.762-0.912). The AUC of ROC curve analysis for GDF15 in synovial fluid samples of SpA versus RA is 0.678 (95% CI, 0.569-0.787).

Different cutoffs with their sensitivities and specificities (and their corresponding 95% CIs) of the GDF15 test for serum are listed in Table 1. Scoring the GDF15 concentration in a serum sample below the respective Cutt-off values allows to identify a patient as an SpA patient with the corresponding sensitivities and specificities.

TABLE 1

Diagnostic performance of GDF15 as serum marker at different cutoffs chosen to obtain different specificities.

| Cut-off concentration (pg/ml) | Sensitivity % (95% CI) | Specificity % (95% CI) |
|---|---|---|
| 900 | 94.3 (88.8-97.6) | 42.1 (32.1-48.2) |
| 800 | 90.0 (84.0-94.5) | 52.6 (41.5-60.9) |
| 700 | 82.9 (76.4-87.8) | 73.7 (61.9-82.8) |
| 600 | 74.3 (67.7-79.4) | 76.3 (64.1-85.7) |
| 500 | 64.3 (57.7-68.6) | 84.2 (72.4-92.1) |
| 400 | 0.5 (45-51.2) | 97.4 (88.1-99.5) |

Example 3

Analysis of Anti-CCP as an Additional RA Marker

The value of the GDF15 marker and anti-CCP as an additional well-known marker was assessed by evaluating the probability to discriminate RA and SpA patients based on different cut-offs of the GDF15 concentration and the presence/absence of a CCP signal. It is generally known that the anti-CCP test has a very high specificity for RA and a relatively low sensitivity to detect an RA patient.

Figure 5:
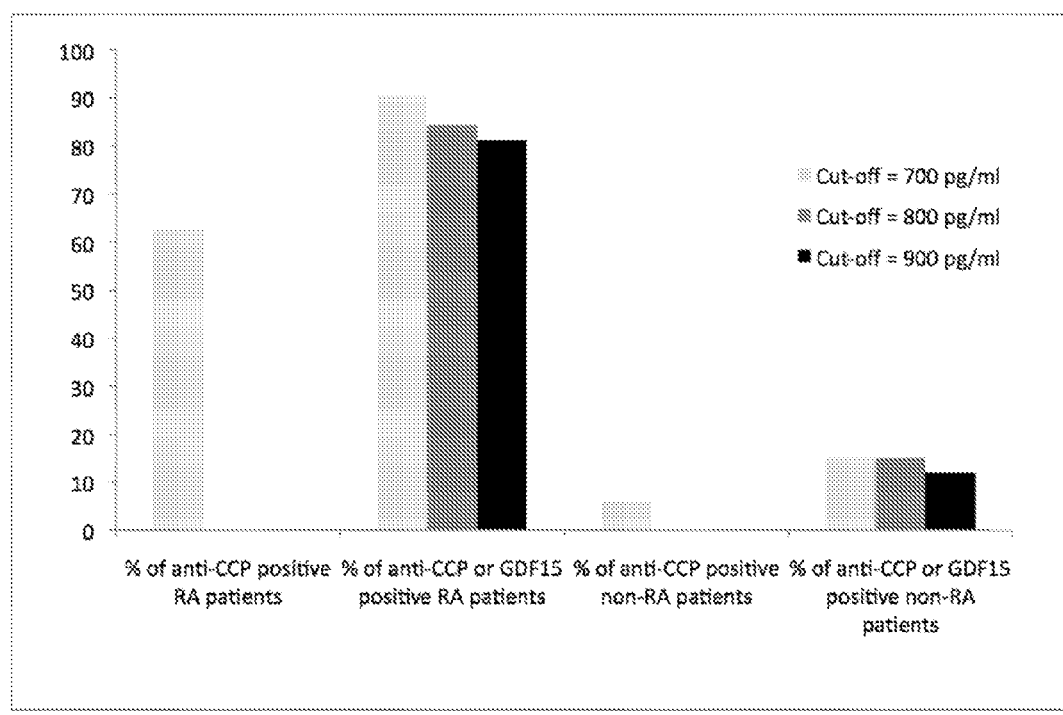
FIG. 5: Evaluation of the value of the GDF15 marker and anti-CCP as an additional well-known marker for the probability to discriminate RA and SpA patients based on different cut-offs of the GDF15 concentration and the presence/absence of a CCP signal.

32 RA and 33 SpA patients were screened for GDF15 serum levels and anti-CCP concentrations. 20 of the 32 clinically diagnosed RA patients were anti-CCP positive. Only 2 clinically diagnosed SpA patients were anti-CCP positive, indicating the high specificity and the rather fair sensitivity of the test. In the group of anti-CCP negative RA patients, GDF15 was applied as an additional criterion: samples below a threshold of 700/800/900 pg/ml were considered as SpA patients and samples above this threshold as non-SpA patients. This showed that 9/7/6 additional true non-SpA patients could be correctly classified. Only 3/3/2 out of 31 anti-CCP negative SpA patients were GDF15 positive. These data indicate that the combination of GDF15 with an additional marker such as anti-CCP test, yields a substantially increased sensitivity to the RA-SpA discriminating test. These data indicate that the combination of GDF15 with an additional marker yields a substantially increased sensitivity to the RA-SpA discriminating test. (FIG. 5)

What is claimed is:

1. A method for diagnosing spondyloarthropathy (SpA) in a human subject comprising:
   i) obtaining a blood serum or synovial fluid sample from said subject;
   ii) performing an immunoassay to detect the presence of growth differentiation factor 15 (GDF15) by applying a monoclonal antibody or fragment thereof specific for GDF15 to said sample, wherein the presence of GDF15 creates an antibody-GDF15 complex;
   iii) applying a detection agent that detects the presence of the antibody-GDF15 complex;
   iv) determining the amount of GDF15 present in said sample; and
   v) for a sample having a GDF15 concentration below a threshold of 700 pg/ml, diagnosing said patient for SpA.

2. The method as claimed in claim 1, wherein the amount of GDF15 is determined in a blood serum sample and a synovial fluid sample, and wherein the ratio of the amount of GDF15 in said serum sample to the amount of GDF15 in said synovial fluid sample correlates to the presence or development of SpA, and wherein the ratio of the amount of GDF-15 in synovial fluid/serum is high in SpA when compared to the same ratio in a subject exhibiting rheumatoid arthritis.

3. The method as claimed in claim 1 wherein determining the amount of GDF15 is further combined with determining one or more markers for inflammatory rheumatic diseases.

4. The method as claimed in claim 1 wherein said GDF15 is part of a marker panel.

5. The method as claimed in claim 1, including determining the presence of anti-CCP and/or RF in said sample, by performing an anti-CCP immunoassay and/or an RF immunoassay.

6. The method as claimed in claim 3, wherein the one or more markers for inflammatory rheumatic diseases are selected from the group consisting of anti-citrullinated protein antibody (anti-CCP) and rheumatoid factor (RF) and wherein said subject sample is a blood sample and the presence of anti-CCP and/or RF is determined in said blood sample.

7. The method of claim 5, wherein the amount of GDF15 is determined in a sample which is negative for anti-CCP and/or RF.

8. The method of claim 1 wherein said immunoassay comprises an enzyme-linked immunosorbent assay (ELISA).

* * * * *